United States Patent
McPherson (10) Patent No.: US 9,636,252 B2
(45) Date of Patent: May 2, 2017

(54) SYSTEMS AND DEVICES FOR TREATMENT OF HYPOTHERMIA AND SYSTEMS INCLUDING GARMENTS ADAPTED TO CONTROLLABLY EMIT ENERGY FOR WARMING WEARER

(71) Applicant: COVIDIEN LP, Mansfield, MA (US)

(72) Inventor: James W. McPherson, Boulder, CO (US)

(73) Assignee: Covidien LP, Mansfield, MA (US)

( * ) Notice: Subject to any disclaimer, the term of this patent is extended or adjusted under 35 U.S.C. 154(b) by 492 days.

(21) Appl. No.: 14/152,495

(22) Filed: Jan. 10, 2014

(65) Prior Publication Data

US 2014/0243938 A1 Aug. 28, 2014

Related U.S. Application Data

(60) Provisional application No. 61/768,990, filed on Feb. 25, 2013.

(51) Int. Cl.

| | | |
|---|---|---|
| A61F 7/00 | (2006.01) | |
| A61F 7/08 | (2006.01) | |
| A61F 7/02 | (2006.01) | |
| A61B 5/01 | (2006.01) | |
| A61B 5/0205 | (2006.01) | |

(52) U.S. Cl.
CPC ............ *A61F 7/02* (2013.01); *A61B 5/01* (2013.01); *A61F 7/007* (2013.01); *A61B 5/02055* (2013.01); *A61F 2007/0002* (2013.01); *A61F 2007/0036* (2013.01); *A61F 2007/0233* (2013.01)

(58) Field of Classification Search
CPC ....... A61N 5/025; A61N 5/0625; A61N 1/403
See application file for complete search history.

(56) References Cited

U.S. PATENT DOCUMENTS

| | | | |
|---|---|---|---|
| 2,831,198 A | 4/1958 | Datlof | |
| 2,911,649 A | 11/1959 | Ruelle et al. | |
| 5,383,918 A | 1/1995 | Panetta | |
| 6,000,395 A | 12/1999 | Brown | |
| 6,278,092 B1 * | 8/2001 | Wu .......................... A43B 3/10 219/212 |
| 6,524,332 B1 | 2/2003 | Augustine et al. | |
| 6,996,848 B2 | 2/2006 | Donaldson | |

(Continued)

FOREIGN PATENT DOCUMENTS

| | | | | |
|---|---|---|---|---|
| EP | 0 287 294 A1 | 10/1988 | | |
| IT | WO 2012110954 A1 * | 8/2012 | ........... | A61B 5/6804 |
| WO | WO 2006/125164 A2 | 11/2006 | | |

*Primary Examiner* — Kaitlyn Smith (57) ABSTRACT

A system for the treatment of hypothermia includes an energy source controllably operable to output energy, a controller operably associated with the energy source, an encasing-structure being conformable over a treatment region, and one or more vital sign detectors adapted to generate an electrical signal indicative of a measurement of a vital sign of a patient. The encasing-structure includes an energy-applicator device including a configuration of energy-delivery elements disposed in association with the encasing-structure. The controller is adapted to receive the electrical signal from the one or more vital sign detectors. The controller is configured to adjust one or more treatment parameters based at least in part on the electrical signal.

18 Claims, 7 Drawing Sheets

(56) References Cited

U.S. PATENT DOCUMENTS

| | | | |
|---|---|---|---|
| 7,766,950 B2* | 8/2010 | Castellani | A43B 7/03 607/108 |
| 7,846,192 B2 | 12/2010 | Panser et al. | |
| 8,359,665 B2 | 1/2013 | Bruce | |
| 8,603,150 B2* | 12/2013 | Kane | A61F 7/02 607/111 |
| 9,008,794 B2* | 4/2015 | Alexandre | A61B 5/6804 607/115 |
| 2003/0040783 A1* | 2/2003 | Salmon | A61F 7/02 607/111 |
| 2003/0069621 A1 | 4/2003 | Kushnir | |
| 2003/0195596 A1* | 10/2003 | Augustine | A61F 7/00 607/104 |
| 2004/0044386 A1* | 3/2004 | Beens | A61N 1/403 607/101 |
| 2006/0107436 A1 | 5/2006 | Donaldson | |
| 2006/0247745 A1 | 11/2006 | Thompson | |
| 2008/0132976 A1* | 6/2008 | Kane | A61F 7/02 607/104 |
| 2008/0234788 A1* | 9/2008 | Wasowski | A43B 7/34 607/104 |
| 2009/0299419 A1* | 12/2009 | West | A61N 5/0625 607/3 |
| 2010/0036369 A1 | 2/2010 | Hancock | |
| 2010/0063556 A1* | 3/2010 | Oestreich | A61B 5/0402 607/3 |
| 2010/0089896 A1* | 4/2010 | Bart | A61F 7/034 219/211 |
| 2010/0094146 A1* | 4/2010 | Coulston | A41D 13/1281 600/499 |
| 2010/0137951 A1* | 6/2010 | Lennox | A61F 7/02 607/104 |
| 2011/0172749 A1* | 7/2011 | Christensen | A61F 7/02 607/104 |
| 2012/0088057 A1 | 4/2012 | Meirowitz et al. | |
| 2012/0089208 A1* | 4/2012 | York | A61N 5/0625 607/100 |
| 2012/0172954 A1* | 7/2012 | Zastrow | A61N 5/025 607/101 |
| 2012/0191164 A1* | 7/2012 | Gander | H05B 3/12 607/96 |
| 2012/0215139 A1* | 8/2012 | Pan | A61N 5/0625 601/15 |
| 2013/0085553 A1* | 4/2013 | Kang | A61N 1/36014 607/100 |
| 2013/0190667 A1* | 7/2013 | Kane | A61F 7/02 601/149 |
| 2014/0024881 A1* | 1/2014 | Alexandre | A61B 5/0022 600/13 |
| 2014/0066786 A1* | 3/2014 | Naghavi | A61B 17/1355 600/481 |
| 2015/0374537 A1* | 12/2015 | Susi | A61F 7/0097 607/104 |

* cited by examiner

SYSTEMS AND DEVICES FOR TREATMENT OF HYPOTHERMIA AND SYSTEMS INCLUDING GARMENTS ADAPTED TO CONTROLLABLY EMIT ENERGY FOR WARMING WEARER

CROSS REFERENCE TO RELATED APPLICATION

The present application claims the benefit of and priority to U.S. Provisional Application Ser. No. 61/768,990, filed on Feb. 25, 2013, the entire contents of which are incorporated herein by reference.

BACKGROUND

1. Technical Field

The present disclosure relates to systems, devices and methods for the treatment of hypothermia. The present disclosure also relates to systems including garments adapted to controllably emit energy for warming the wearer, e.g., to maintain the core body temperature.

2. Discussion of Related Art

Normal body core temperature is controlled within tight parameters to ensure normal metabolism and body functions, such as nervous system function, e.g., the conduction of nerve impulses, and optimal skeletal muscle contraction. Body temperature is usually maintained near a constant level of 36.5° C. to 37.5° C. (98° F. to 100° F.) through biologic homeostasis or thermoregulation. Thermoregulation is the process of maintaining normal core temperature within certain boundaries and involves positive and negative feedback by the brain to minimize variations from normal values or thresholds. If the body is unable to maintain a normal temperature and core temperature decreases below normal levels, a condition known as hypothermia occurs.

Hypothermia is a serious condition in which the core body temperature drops to below the level required for normal metabolism and body functions, generally a temperature of less than 36° C. (96.8° F.), where tissue damage or death may occur. As core body temperature decreases, the basal metabolic rate and oxygen consumption drop. Hypothermia may be classified as mild hypothermia (34° C. to 36° C.), moderate hypothermia (32° C. to 34° C.), and severe hypothermia (below 32° C.).

Hypothermia affects the function of all organ systems. As the core body temperature declines, there can be respiratory depression with resultant hypoxemia and hypercarbia. Hypoxemia refers to a low level of oxygen in the blood. Hypercarbia refers to high arterial carbon dioxide ($CO_2$) levels. A combined respiratory and metabolic acidosis, e.g., high acidity of blood and tissue fluids, may occur due to hypoventilation, $CO_2$ retention, reduced hepatic metabolism of organic acid due to decreased perfusion of the liver, and increased lactic acid production from impaired perfusion of skeletal muscle and shivering. Shivering, if prolonged, may cause hypoglycemia.

Hypothermia contributes to alterations in physiologic functions, and through alterations of the normal coagulation function, can contribute to further hemorrhage (excessive bleeding over a short period of time, either internally or externally) and shock in an injured victim. Severe accidental hypothermia is associated with marked depression of cerebral blood flow and oxygen requirement, reduced cardiac output, and decreased arterial pressure. Hypothermia following exposure with core temperature below 32° C. is associated with high mortality.

Rewarming of hypothermic patients may be undertaken using passive and/or active methods. Active core rewarming techniques are the primary therapeutic modality in hypothermic victims in cardiac arrest or unconscious hypothermic patients with a slow heart rate. Active core rewarming includes external methods of rewarming as well as methods directed at rewarming the core. One simple means of transferring a large amount of heat to the core of victims with moderate to severe hypothermia is the administration of warmed intravenous fluids. External rewarming methods include the use of heat packs; heating blankets, such as warm-air-circulating blankets and warm-fluid-circulating blankets; reflective blankets; and radiant heat shields.

Passive rewarming methods generally include optimizing environmental conditions while allowing the victim's own heat-generating capabilities to restore normal core temperature. Passive rewarming methods used in mildly hypothermic victims and as an adjunct in moderate-to-severe hypothermia include increasing ambient room temperature and blanket coverage.

Avoiding hypothermia in the perioperative environment is an ongoing challenge. Patients can develop hypothermia perioperatively as a result of various factors in the perioperative environment or the thermoregulatory response of the body to anesthetic agents. Inadvertent perioperative hypothermia is associated with serious complications involving circulation of blood, coagulation, wound healing, and drug metabolism.

First and emergency responders, such as prehospital and EMS providers, firefighters, and police officers, and active military personnel must be careful about their own health and physical abilities in order to perform their job functions well. Decreases in core body temperature may reduce work capacity, stamina, cognitive functioning, and efficiency and can lead to individual morbidity and mortality.

SUMMARY

According to an aspect of the present disclosure, a system for the treatment of hypothermia is provided. The system includes an energy source controllably operable to output thermal energy, a controller operably associated with the energy source, an encasing-structure conformable over a treatment region, and one or more vital sign detectors adapted to generate an electrical signal indicative of a measurement of a vital sign of a patient. The encasing-structure includes an energy-applicator device including a configuration of energy-delivery elements disposed in association with the encasing-structure. The controller is adapted to receive the electrical signal from the one or more vital sign detectors and generate an energy response thereto. The controller is configured to adjust one or more treatment parameters based at least in part on the electrical signal.

According to an aspect of the present disclosure, a system including a body-enclosing garment adapted to controllably emit energy for warming the wearer is provided. The body-enclosing garment includes an energy-applicator device including a configuration of one or more energy-delivery element arrays disposed in association with the body-enclosing garment. The system also includes a controller operably associated with a signal generator and a plurality of vital sign detectors. Each one of the plurality of vital sign detectors is adapted to generate one or more electrical signals indicative of a measurement of a vital sign of the wearer. The controller is adapted to receive the one or more electrical signals from the plurality of vital sign detectors. The controller is configured to selectively control the one or more energy-delivery element arrays to deliver energy over one or more regions of the wearer based at least in part on the one or more electrical signals received from the plurality of vital sign detectors.

BRIEF DESCRIPTION OF THE DRAWINGS

Objects and features of the presently-disclosed systems, devices and methods for the treatment of hypothermia and systems including garments adapted to controllably emit energy for warming the wearer will become apparent to those of ordinary skill in the art when descriptions of various embodiments thereof are read with reference to the accompanying drawings, of which.

DETAILED DESCRIPTION

Hereinafter, embodiments of the presently-disclosed systems, devices and methods for the treatment of hypothermia and embodiments of the presently-disclosed systems including garments adapted to controllably emit energy for warming the wearer are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the device, or component thereof, closer to the user and the term "distal" refers to that portion of the device, or component thereof, farther from the user.

This description may use the phrases "in an embodiment," "in embodiments," "in some embodiments," or "in other embodiments," which may each refer to one or more of the same or different embodiments in accordance with the present disclosure.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used herein, "radio frequency" or "RF" generally refers to electromagnetic waves having a lower frequency than microwaves. As it is used in this description, "energy applicator" generally refers to any device that can be used to transfer energy from a power generating source, such as a microwave or RF electrosurgical generator, to tissue.

As it is used in this description, "transmission line" generally refers to any transmission medium that can be used for the propagation of signals from one point to another. A transmission line may be, for example, a wire, a two-wire line, a coaxial wire, and/or a waveguide. Transmission lines such as microstrip, coplanar waveguide, stripline or coaxial may also be considered to be waveguides.

As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or submultiple of the wavelength of an electromagnetic wave or electrical signal propagating within a transmission medium. The wavelength may be expressed in radians or in artificial units of angular measure, such as degrees. The electric length of a transmission medium may be expressed as its physical length multiplied by the ratio of (a) the propagation time of an electrical or electromagnetic signal through the medium to (b) the propagation time of an electromagnetic wave in free space over a distance equal to the physical length of the medium. The electrical length is in general different from the physical length. By the addition of an appropriate reactive element (capacitive or inductive), the electrical length may be made significantly shorter or longer than the physical length.

As it is used in this description, "amplifier" generally refers to a device that produces an electrical output that is a function of the corresponding electrical input parameter, and increases the magnitude of the input by means of energy drawn from an external source (e.g., it introduces gain), or in some situations it is possible that the amplifier may have a gain of zero or unity gain. In general, a gain (amplification) is expressed as a positive decibel value, a loss (attenuation) is expressed as a negative decibel value, and unity gain (no gain) is expressed as zero decibels. In a power amplifier, the gain is usually defined as the ratio of the power output to the power input of the amplifier.

As it is used herein, "electrical circuit" or simply "circuit" generally refers to a combination of a number of electrical devices and conductors that when connected together, form a conducting path to fulfill a desired function. Any constituent part of an electrical circuit other than the interconnections may be referred to as a "circuit element."

As it is used in this description, "user interface" generally refers to any visual, graphical, tactile, audible, sensory or other mechanism for providing information to and/or receiving information from a user or other entity. The term "user interface" as used herein may refer to an interface between a human user (or operator) and one or more devices to enable communication between the user and the device(s). Examples of user interfaces that may be employed in various embodiments of the present disclosure include without limitation, switches, potentiometers, buttons, dials, sliders, a mouse, keyboard, keypad, joysticks, trackballs, display screens, various types of graphical user interfaces (GUIs), touch screens, microphones and other types of sensors or devices that may receive some form of human-generated stimulus and generate a signal in response thereto.

As it is used herein, "computer" generally refers to anything that transforms information in a purposeful way. For the purposes of this description, the term "code" should be interpreted as being applicable to software, firmware, or a combination of software and firmware.

As it is used in this description, "vital signs" generally includes the measurement of: temperature, respiratory rate, pulse rate, pulse pressure, blood pressure, mean arterial pressure and, where appropriate, blood oxygen saturation.

Various embodiments of the present disclosure provide systems, devices and methods for the treatment of hypothermia. Various embodiments of the present disclosure provide microwave apparatus operable to emit energy absorbable into the body of a patient for the treatment of hypothermia. Embodiments may be implemented using electromagnetic radiation at microwave frequencies or at other frequencies. A system including an energy-applicator device including energy-delivery elements integrated into an encasing-structure, according to various embodiments, is configured to operate between about 300 MHz and about 10 GHz.

Various embodiments of the present disclosure provide systems including body-enclosing garments adapted to maintain core body temperature of the wearer. Various embodiments of the presently-disclosed systems including body-enclosing garments are adapted to monitor one or more vital sign sensors and/or generate a measure of the core body temperature based, at least in part, on one or more electrical signals outputted by the one or more sensors.

Various embodiments of the present disclosure provide systems including an energy-applicator device and one or more sensors operably associated with a controller to allow for patient monitoring, e.g., core temperature monitoring, to facilitate feedback-control of emitted energy. Various embodiments of the presently-disclosed systems including an energy applicator conformable over a treatment region of a patient are suitable for monitoring and/or controllably increasing the patient's core body temperature.

Figure 1:
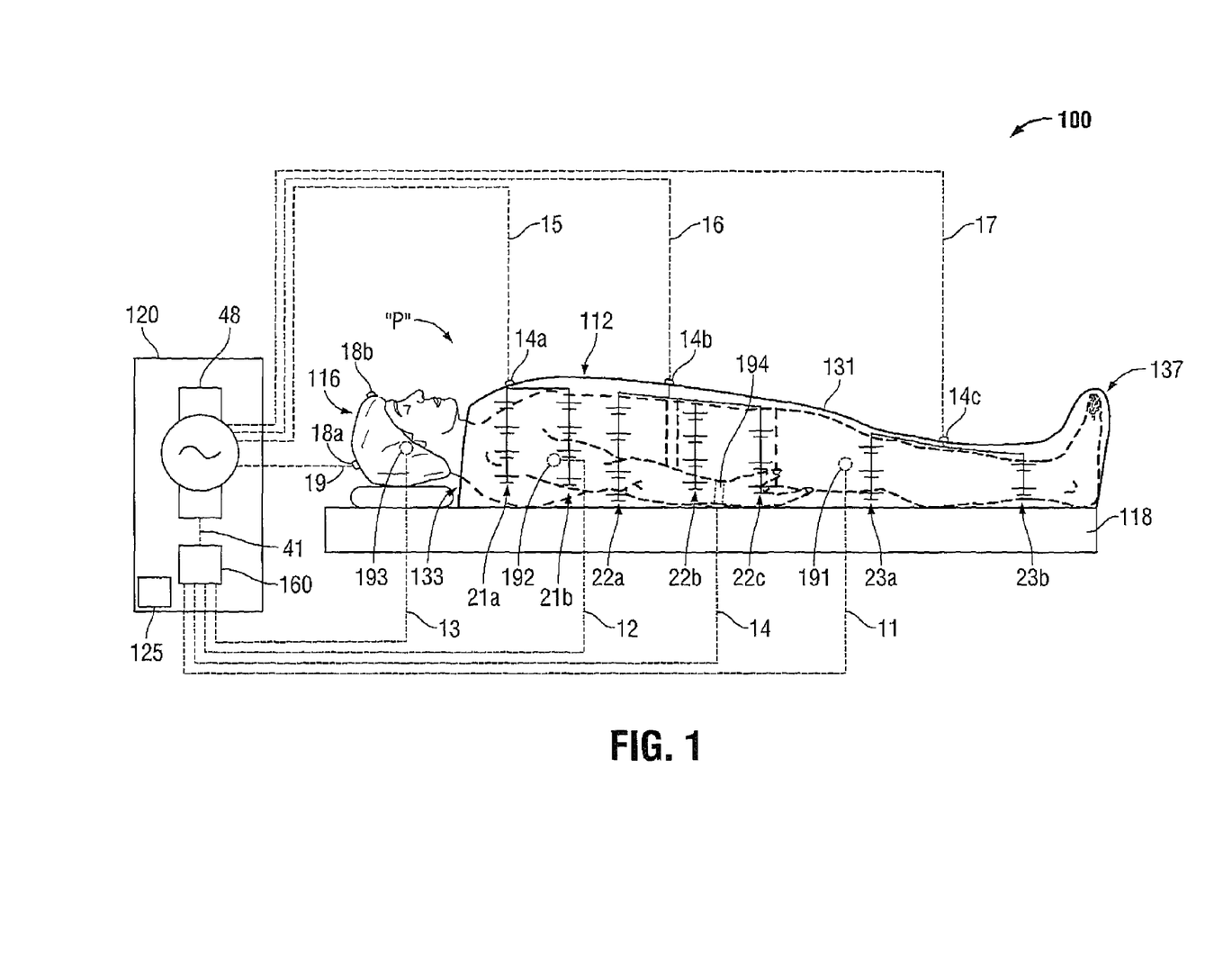
FIG. 1 is a schematic diagram of a system including a first energy-applicator device adapted to radiate electromagnetic energy for warming a patient, such as for hypothermia treatment, shown with an optional second energy-applicator device, in accordance with an embodiment of the present disclosure.

FIG. 1 shows a system (shown generally as 100) operable to emit energy absorbable into the body of a patient "P" to increase core body temperature in accordance with an embodiment of the present disclosure. System 100 includes an energy source 120 controllably operable to output energy, e.g., microwave energy, and a controller 160 operably associated with the energy source 120. System 100 includes a first energy-applicator device 112 including a configuration of energy-delivery elements integrated into an encasing-structure 131 conformable over a treatment region of the patient "P". In some embodiments, the encasing-structure 131 is adapted to controllably emit a near-field standing wave of energy absorbable into the body, or portion thereof, of the patient "P" to increase core body temperature.

System 100 may additionally include a second energy-applicator device 116. In some embodiments, the second energy-applicator device 116 includes a first electrical connector 18a suitable for making an electrical connection with a transmission line 19, and may include a second electrical connector 18b.

One or more vital sign detectors, e.g., for locating on the skin and/or within a body cavity, may be communicatively-coupled to the controller 160. In various embodiments, the controller 160 may be configured to monitor and/or controllably increase core body temperature and/or adjust treatment parameters and/or cause cessation of energy delivery from the energy source 120 through the first energy-applicator device 112 to the treatment region of the patient "P" based, at least in part, on one or more signals (e.g., indicative of temperature, respiratory rate, pulse rate, pulse pressure, pulse oximetry, mean arterial pressure and/or blood pressure) received from one or more vital sign detectors.

First energy-applicator device 112 may be adapted to be electrically-coupled to the energy source 120. One or more transmission lines may be provided to electrically-couple the first energy-applicator device 112 to the energy source 120. In some embodiments, as shown in FIG. 1, the encasing-structure 131 includes electrical connectors 14a, 14b and 14c suitable for making electrical connections with transmission lines 15, 16 and 17, respectively. Electrical connectors 14a, 14b and 14c may be adapted to be removeably coupleable to the transmission lines 15, 16 and 17, respectively.

Energy source 120 may be any generator suitable for use with the first energy-applicator device 112 and may be configured to provide various frequencies of energy. In some embodiments, as shown in FIG. 1, the energy source 120 includes a signal generator 48 capable of generating high-frequency signals, e.g., microwave signals. In alternative embodiments, the energy source 120 may include a plurality of signal generators. In some embodiments, the energy source 120 is configured to provide microwave energy at an operational frequency from about 300 MHz to about 10 GHz. Energy source 120 may include one or more signal amplifiers (not shown) operable to amplify the signal, e.g., microwave signal, to a desirable power level. Various components of the energy source 120 may be communicatively-coupled to the controller 160. In some embodiments, as shown in FIG. 1, a transmission line 41 is provided to electrically-couple the signal generator 48 to the controller 160.

Energy source 120 may include a power generation circuit that generates and provides DC power from a DC power supply. In some embodiments, wherein the signal generator 48 is a microwave signal generator, DC power from the DC power supply and the microwave signal from the signal generator 48 are supplied to a microwave amplifier unit that amplifies the microwave signal to a desirable power level. The microwave amplifier unit may include one or more power amplifiers to amplify the microwave signal generated by the signal generator 48 to a desired energy level.

In some embodiments, the energy source 120 includes a user interface 125, e.g., configured to provide user-input capabilities and/or capabilities for simplified use and/or programming of the energy source 120. The user interface 125 may be adapted to enable a user to selectively configure one or more operating parameters of the energy source 120, or component thereof, e.g., to achieve a desired core body temperature. The user interface 125 may include a screen (not shown), such as a flat-panel display, e.g., an LCD (liquid crystal display), plasma display panel (PDP), organic light emitting diode (OLED), or electro-luminescent display (ELD). The screen may be communicatively-coupled to the controller 160. In alternative embodiments, the user interface may be attached, coupled to, or otherwise associated with, the encasing-structure 131.

Controller 160 may include any type of computing device, computational circuit, or any type of processor or processing circuit capable of executing a series of instructions that are stored in a memory (not shown) of the controller 160. Controller 160 may be disposed within, or otherwise associated with, the energy source 120. Controller 160 may be attached, coupled to, or otherwise associated with, the first energy-applicator device 112, or component thereof, e.g., encasing-structure 131. Controller 160 may be a standalone unit.

In some embodiments, the system 100 may include one more vital sign detectors. In some embodiments, the controller may be adapted to adjust one or more treatment parameters based, at least in part, on one or more signals received from one or more vital sign detectors (e.g., first sensor device 191, second sensor device 192, third sensor device 193, and/or fourth sensor device 194 shown in FIG. 1). Some examples of treatment parameters include the duration of application of electromagnetic energy by the one or more energy-delivery elements (or groups or arrays of energy-delivery elements), the power level of energy delivered to one or more regions of the encasing-structure 131 and/or other energy-delivery apparatus (e.g., second energy-applicator device 116 shown in FIG. 1), the level to which core body temperature is raised, and/or the rate of increase in core body temperature.

Controller 160 may be configured to receive an electrical signal and to generate a measure of the vital sign based at least in part on the received signal, e.g., to facilitate feedback-control of emitted energy. Some examples of vital sign detectors in accordance with embodiments of the present disclosure include temperature sensors, sensor devices used to detect blood pressure, pulse pressure, mean arterial pressure, and/or pulse rate, sensor devices adapted to sense respiratory rate, sensor devices adapted to sense pulse oximetry and/or sensor devices adapted to sense an arterial pulse (e.g., adapted to be placed against an anatomical location of the patient "P" within which is an artery).

System 100 may include any suitable configuration of one or more sensor devices. In some embodiments, the system 100 includes one or more sensor devices adapted to generate an electrical signal indicative of a sensed temperature of a region of the body of the patient "P". In some embodiments, a closed loop control mechanism, such as a feedback controller with a microprocessor, may be implemented for controlling the delivery of energy, e.g., microwave energy, to the patient "P" based on one or more electrical signals outputted by one or more temperature sensors, singly, or in combination with other vital sign sensors (e.g., sensor devices adapted to detect blood pressure, pulse pressure, mean arterial pressure, and/or pulse rate, sensor devices adapted to sense respiratory rate, sensor devices adapted to sense pulse oximetry and/or sensor devices adapted to sense an arterial pulse).

In some embodiments, the system 100 includes a first sensor device 191 adapted to generate an electrical signal indicative of a sensed temperature of a first region of the body of the patient "P", and may include a second sensor device 192 adapted to generate an electrical signal indicative of a sensed temperature of a second region of the body of the patient "P". In some embodiments, the system 100 additionally includes a third sensor device 193 adapted to generate an electrical signal indicative of a sensed temperature of a third region of the body of the patient "P".

In some embodiments, as shown in FIG. 1, the system 100 includes a first sensor device 191 located within the groin area of the patient "P", a second sensor device 192 located within an armpit of the patient "P", and a third sensor device 193 located within an ear canal of the patient "P". First sensor device 191, the second sensor device 192, and/or the third sensor device 193 may include any suitable type of device capable of generating a signal indicative of a temperature of a medium in contact therewith. System 100 may include fewer or additional sensors than the first sensor device 191, the second sensor device 192, and the third sensor device 193 shown in FIG. 1.

In some embodiments, the first sensor device 191, the second sensor device 192, and/or the third sensor device 193 may be a thermocouple, thermistor, hall effect device, forward-biased diode, optical fiber, or any other type of temperature sensing device capable of sending a signal indicative of a temperature. A thermocouple is a junction between two different metals that produces a voltage related to a temperature difference. Thermocouples are made of specific alloys, which in combination have a predictable and repeatable relationship between temperature and voltage. Different alloys may be used for different temperature ranges and to resist corrosion. A thermistor is a type of resistor whose resistance varies with temperature. Thermistors are commonly made with ceramic or polymer materials. The Hall effect sensor is a magnetic field sensor, which can be used as the principle component in many other types of sensing devices. Hall effect based sensing devices can be used for sensing temperature. The voltage drop across a forward-biased diode varies only slightly with the current, and is a function of temperature; this effect can be used as a temperature sensor.

First sensor device 191, the second sensor device 192, and/or the third sensor device 193 may include a wireless communication device, e.g., adapted to provide wireless data communications with the controller 160. In some embodiments, as shown in FIG. 1, the first sensor device 191 is electrically-coupled via a transmission line 11 to the controller 160, the second sensor device 192 is electrically-coupled via a transmission line 12 to the controller 160, and the third sensor device 193 is electrically-coupled via a transmission line 13 to the controller 160.

In some embodiments, as shown in FIG. 1, the system 100 includes a fourth sensor device 194, e.g., strapped to the patient's wrist. In some embodiments, the fourth sensor device 194 may be adapted to detect blood pressure and/or adapted to sense an arterial pulse. Fourth sensor device 194, which may be located at any suitable location on the body of the patient "P", may include any device capable of generating a signal indicative of a vital sign. System 100 may include additional, fewer, or different sensors than shown in FIG. 1.

In some embodiments, the first sensor device 191 is adapted to sense a temperature of the patient "P" to facilitate feedback-control of emitted energy, and the second sensor device 192 may be adapted to sense the arterial pulse of the patient "P" to facilitate feedback-control of emitted energy. In some embodiments, the second sensor device 192 may be adapted to detect the blood pressure of the patient "P" to facilitate feedback-control of emitted energy.

In some embodiments, wherein the system includes a third sensor device 193, the third sensor device 193 may be adapted to sense the pulse oximetry of the patient to facilitate feedback-control of emitted energy.

Based on one or more signals generated by the first sensor device 191, the second sensor device 192, the third sensor device 193, and/or the fourth sensor device 194, the controller and/or other circuitry (not shown) may adjust one or more operating parameters associated with the energy source 120 and/or perform other control functions, alarming functions, or other functions in association therewith. Controller 160 may include logic, circuitry and/or code adapted to control one or more operating parameters associated with the energy source 120 responsive to one or more electrical signals received from a single sensor device or a plurality of sensor devices. Some examples of operating parameters associated with the energy source 120 that may be adjusted include temperature, impedance, power, current, voltage, mode of operation, and duration of application of electromagnetic energy.

System 100 may be adapted to provide various configurations of electrical connections between the first energy-applicator device 112, or component thereof (e.g., electrical connectors 14*a*, 14*b* or 14*c*), the energy source 120, or component thereof (e.g., amplifier 48), the controller 160, the first sensor device 191, the second sensor device 192, the third sensor device 193, and/or the fourth sensor device 194. It is to be understood that the light dashed-lines indicative of electrical connections between various components of the system 100 shown in FIG. 1 are merely illustrative and non-limiting examples of electrical connections, and that system embodiments of the present disclosure may utilize many different configurations of electrical connections, some with fewer, or additional, electrical connections than depicted in FIG. 1.

First energy-applicator device 112 may include various configurations of groups or arrays of energy-delivery elements. In some embodiments, as shown in FIG. 1, the energy-delivery elements of the first energy-applicator device 112 are configured to define a plurality of energy-delivery element arrays 21*a*, 21*b*, 22*a*, 22*b*, 22*c*, 23*a* and 23*b* operable to emit energy absorbable into the body of a patient "P" to increase core body temperature. In some embodiments, one or more vital sign detectors may be disposed in association with one or more energy-delivery element arrays, or portions thereof, and the controller 160 may be configured to active and deactivate individual energy-delivery element arrays, or portions thereof, and/or adjust one or more operating parameters associated with the energy source 120 responsive to one or more signals received from the vital sign detectors.

The encasing-structure 131 is formed of a material, or combination of materials, suitable for use to support or house a configuration of energy-delivery elements (e.g., energy-delivery element arrays 21*a*, 21*b*, 22*a*, 22*b*, 22*c*, 23*a* and 23*b* shown in FIG. 1). The encasing-structure 131 may be formed of any suitable conformable material that allows the energy-delivery elements to radiate electromagnetic energy to the treatment region, and may have a single-layer or multi-layer construction. In some embodiments, the encasing-structure 131 may include one or more layers of dielectric material. In some embodiments, dielectric materials used to form the encasing-structure 131 may vary in dielectric constant, e.g., to aid in radiation directivity and impedance matching and/or to achieve the optimum energy to tissue delivery. In some embodiments, the energy-delivery elements (or energy-delivery element arrays) may be disposed between the same or different layers of dielectric material. In some embodiments, the energy-delivery elements (or energy-delivery element arrays) may be disposed on an outward-facing surface of the encasing-structure 131.

Figure 2:
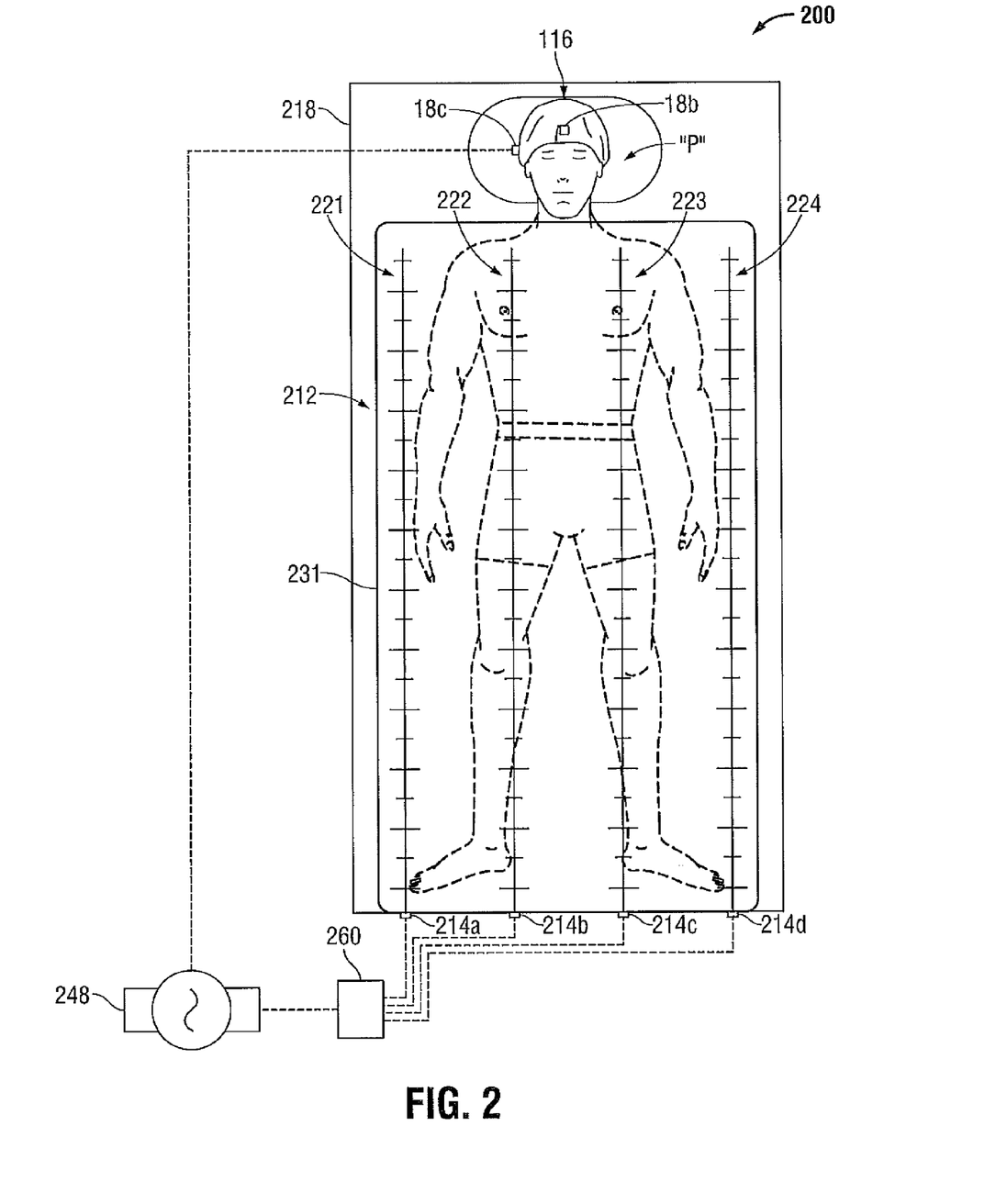
FIG. 2 is a schematic diagram of a system including another embodiment of a first energy-applicator device adapted to radiate electromagnetic energy for warming a patient, such as for hypothermia treatment, shown with the (optional) second energy-applicator device of FIG. 1, in accordance with the present disclosure.

FIG. 2 shows a system (shown generally as 200) operable to emit energy absorbable into the body of a patient "P" to increase core body temperature in accordance with an embodiment of the present disclosure. System 200 includes a signal generator 248 capable of generating high-frequency signals, e.g., microwave signals, and a controller 260 operably associated with the signal generator 248. System 200 includes a first energy-applicator device 212 including a configuration of energy-delivery elements integrated into an encasing-structure 231 conformable over a treatment region of the patient "P".

In some embodiments, the encasing-structure 231 is adapted to controllably emit a near-field standing wave of energy absorbable into the body, or portion thereof, of the patient "P" to increase core body temperature. The encasing-structure 231 may include one or more layers of dielectric material, and may be formed similar to the encasing-structure 131 shown in FIG. 1.

In some embodiments, the system 200 includes one or more sensor devices adapted to generate an electrical signal indicative of a sensed temperature of a region of the body of the patient "P". Controller 260 may include logic, circuitry and/or code adapted to control one or more operating parameters associated with the signal generator 248 responsive to one or more electrical signals received from one or more sensor devices.

First energy-applicator device 212 may include one or more groups or arrays of energy-delivery elements operable to emit energy absorbable into the body of the patient "P" to increase core body temperature. In some embodiments, as shown in FIG. 2, the energy-delivery elements of the first energy-applicator device 212 are configured as four energy-delivery element arrays 221, 222, 223 and 224, longitudinally extending along the reclining patient height. In some embodiments, one or more vital sign detectors may be disposed in association with one or more energy-delivery element arrays, or portions thereof, and the controller 260 may be configured to active and deactivate one or more energy-delivery element arrays, or portions thereof, and/or adjust one or more operating parameters associated with the signal generator 248 responsive to one or more signals received from the vital sign detectors.

First energy-applicator device 212 may be adapted to be electrically-coupled to the signal generator 248. One or more transmission lines may be provided to electrically-couple the first energy-applicator device 212 to the signal generator 248. In some embodiments, as shown in FIG. 2, the encasing-structure 231 includes electrical connectors 214*a*, 214*b*, 214*c* and 214*d* suitable for making electrical connections with transmission lines. Electrical connectors 214*a*, 214*b*, 214*c* and 214*d* may be adapted to be removeably coupleable to the transmission lines. The shape, size, number and location of the electrical connectors may be varied from the configuration depicted in FIG. 2.

Figure 3:
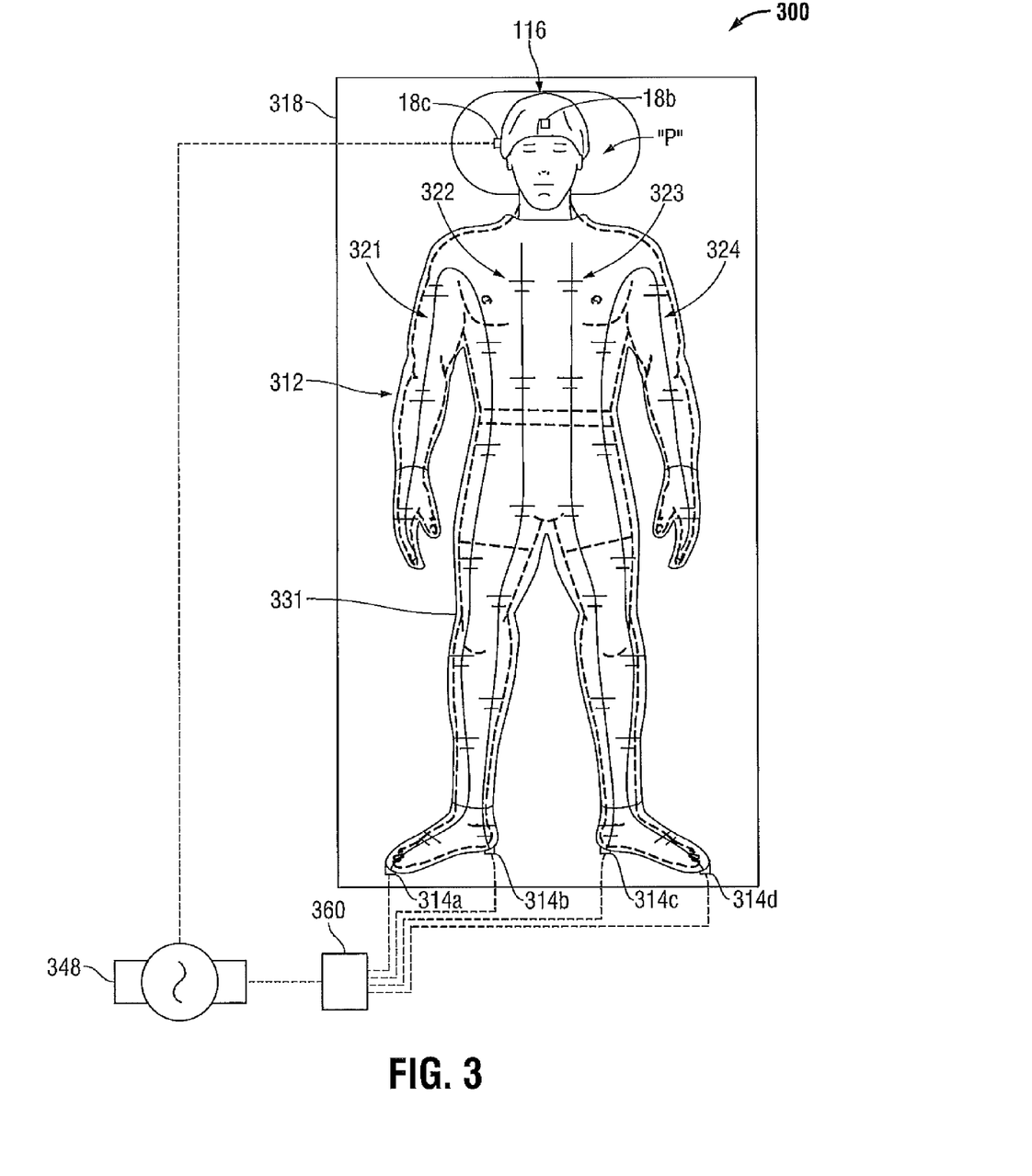
FIG. 3 is a schematic diagram of a system including yet another embodiment of a first energy-applicator device adapted to radiate electromagnetic energy for warming a patient, such as for hypothermia treatment, shown with the (optional) second energy-applicator device of FIG. 1, in accordance with the present disclosure.

Signal generator 248 and the controller 260 shown in FIG. 2 are similar to the signal generator 48 and the controller 160, respectively, shown in FIG. 1, and further description thereof is omitted in the interests of brevity. In some embodiments, the system 200 may include the energy source 120 shown in FIG. 1. System 200 may additionally include the second energy-applicator device 116 shown in FIG. 1. In some embodiments, as shown in FIGS. 2 and 3, the second energy-applicator device 116 may include a third electrical connector 18*c* suitable for making an electrical connection with a transmission line. It is to be understood that the system 200 may include any of the components and/or electrical connections of the system 100 shown in FIG. 1.

FIG. 3 shows a system (shown generally as 300) operable to emit energy absorbable into the body of a patient "P" to increase core body temperature in accordance with an embodiment of the present disclosure. System 300 includes a first energy-applicator device 312 including a configuration of energy-delivery elements integrated into a body-fitting member 331. In some embodiments, the body-fitting member 331 is adapted to controllably emit a near-field standing wave of energy absorbable into the body, or portion thereof, of the patient "P" to increase core body temperature.

System 300 includes a signal generator 348 capable of generating high-frequency signals, e.g., microwave signals, and a controller 360 operably associated with the signal generator 348. One or more transmission lines may be provided to electrically-couple the first energy-applicator device 312 to the controller 360 and/or the signal generator 348. In some embodiments, the body-fitting member 331 may be adapted to allow the first energy-applicator device 312 to be electrically-coupled to the controller 360 and/or the signal generator 348.

Body-fitting member 331 may be formed of one or more layers of any suitable material to enclose the torso, arms and legs of the patient "P", and may be conformable to fit the body contours. Body-fitting member 331 may have a single layer or multi-layer construction, and may include any suitable dielectric material. Body-fitting member 331 may include one or more fasteners (e.g., zippered fasteners, adjustable hook-and-clasp fastening means, such as Velcro, drawstrings, etc.) to allow the body-fitting member 331 to be readily applied to patients, e.g., non-ambulatory patients. In some embodiments, the body-fitting member 331 may be provided with one or more fasteners extending along either, or both, lateral sides thereof. In some embodiments, as shown in FIG. 3, the body-fitting member 331 includes hand-enclosure portions and foot-enclosure portions adapted to enclose both hands and feet of the patient "P". In alternative embodiments, the body-fitting member 331 may be configured to enclose the arms above the wrists and/or to enclose the legs above the ankles.

First energy-applicator device 312 may include one or more groups or arrays of energy-delivery elements operable to emit energy absorbable into the body of the patient "P" to increase core body temperature. In some embodiments, as shown in FIG. 3, the energy-delivery elements of the first energy-applicator device 312 are configured as four energy-delivery element arrays 321, 322, 323 and 324, longitudinally extending along the reclining patient height.

In some embodiments, as shown in FIG. 3, the encasing-structure 331 includes electrical connectors 314a, 314b, 314c and 314d suitable for making electrical connections with transmission lines. Electrical connectors 314a, 314b, 314c and 314d may be adapted to be removeably coupleable to the transmission lines. The shape, size, number and location of the electrical connectors may be varied from the configuration depicted in FIG. 3. In an alternative embodiment, the encasing-structure 331 may be provided with two electrical connectors, e.g., a first electrical connector associated with the first and second energy-delivery element arrays 321 and 322, and a second electrical connector associated with the third and fourth energy-delivery element arrays 323 and 324.

Controller 360 may be configured to receive an electrical signal from one or more vital sign detectors. In some embodiments, one or more vital sign detectors may be disposed in association with one or more energy-delivery element arrays, or portions thereof, and the controller 360 may be configured to active and deactivate one or more energy-delivery element arrays, or portions thereof, and/or adjust one or more operating parameters associated with the signal generator 348 responsive to one or more signals received from the vital sign detectors.

System 300 may be adapted to provide various configurations of electrical connections between the first energy-applicator device 312, or component thereof (e.g., energy-delivery element arrays 321, 322, 323 and 324), the body-fitting member 331, or component thereof (e.g., electrical connectors 314a, 314b, 314c and 314d), the signal generator 348, and the controller 360, and/or one or more vital sign detectors.

Signal generator 348 may be configured to provide various frequencies of energy. In some embodiments, the system 300 may include the energy source 120 shown in FIG. 1. System 300 may additionally include the second energy-applicator device 116 shown in FIG. 1. It is to be understood that the system 300 may include any of the components and/or electrical connections of the system 100 shown in FIG. 1 and/or the system 200 shown in FIG. 2.

Figure 4:
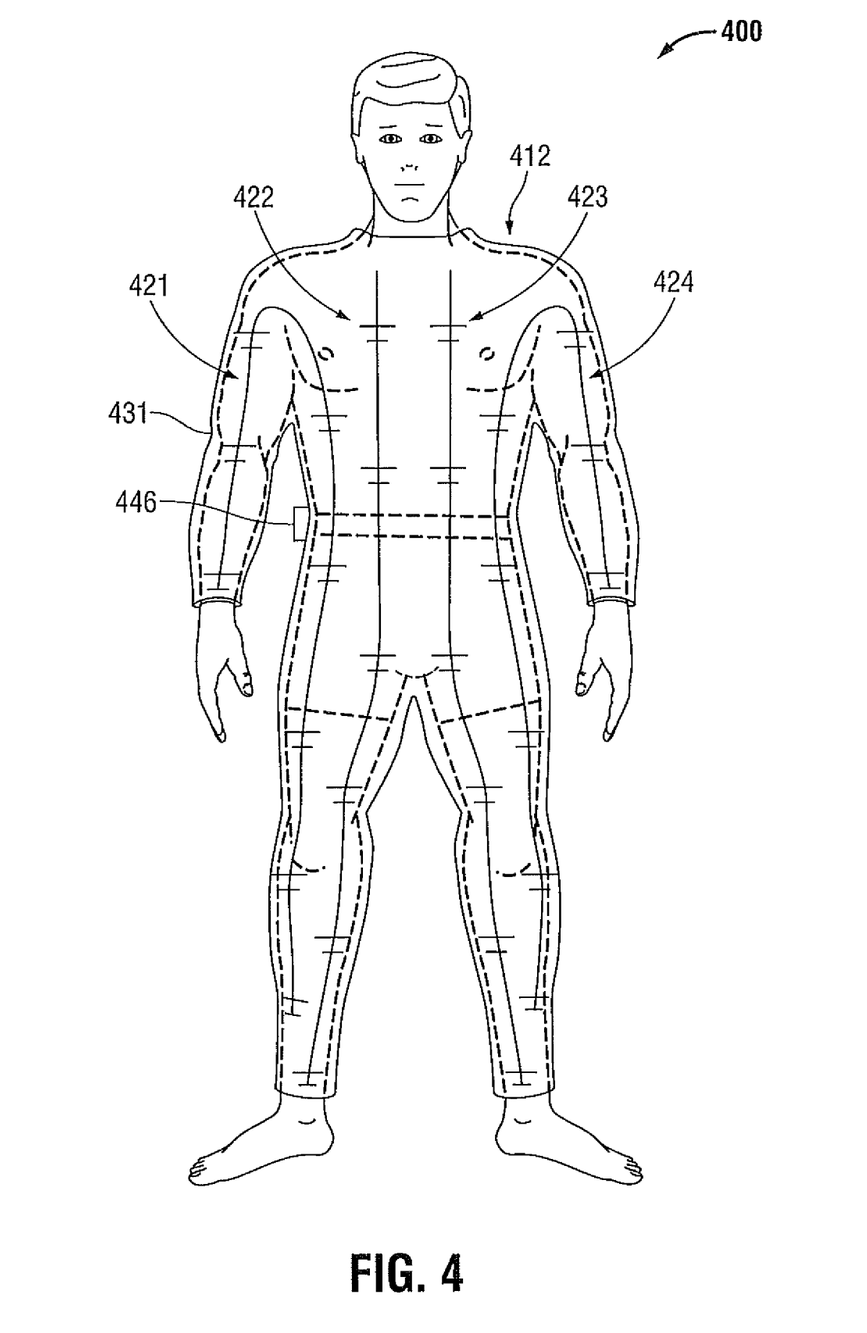
FIG. 4 is a schematic diagram of a system including a body-enclosing garment adapted to radiate electromagnetic energy for warming a wearer in accordance with an embodiment of the present disclosure.

FIG. 4 shows a system (shown generally as 400) including a body-enclosing garment 431 adapted to radiate electromagnetic energy for warming the wearer in accordance with an embodiment of the present disclosure. Body-enclosing garment 431 includes an energy-applicator device 412 including a configuration of energy-delivery elements integrated into the body-enclosing garment 431. System 400 includes a power-supply/controller module 446. In some embodiments, the power-supply/controller module 446 is capable of generating high-frequency signals, e.g., microwave signals. In some embodiments, the body-enclosing garment 431 is adapted to controllably emit a near-field standing wave of energy absorbable into the body of the wearer.

Body-enclosing garment 431 may be provided with a configuration of electrical connections adapted to electrically-couple the energy-applicator device 412 to the power-supply/controller module 446. System 100 may additionally, or alternatively, be adapted to selectively enable the power-supply/controller module 446 to receive signals from a remote signal generator, e.g., a standalone signal generator.

System 400 may include one or more sensors, e.g., communicatively-coupled to the power-supply/controller module 446, and/or communicatively-coupled to an external device or system (e.g., remote monitoring system). In some embodiments, the system 400 may include one or more vital sign sensors adapted to be placed against an anatomical location and/or within a body cavity. One or more sensor devices, in their entirety, or in part, may additionally, or alternatively, be coupled to or otherwise associated with the body-enclosing garment 431. In some embodiments, the system 400 includes one or more temperature sensors operably associated with the power-supply/controller module 446, singly, or in combination with other vital sign sensors (e.g., devices adapted to detect blood pressure, pulse pressure, mean arterial pressure, and/or pulse rate, sensor devices adapted to sense respiratory rate, sensor devices adapted to sense pulse oximetry and/or adapted to sense an arterial pulse), to allow for monitoring, e.g., core temperature monitoring, to facilitate feedback-control of emitted energy.

In some embodiments, the power-supply/controller module 446 includes a controller operably associated with a signal generator capable of generating high-frequency signals, e.g., microwave signals, and may include an amplifier adapted to amplify a high-frequency input signal to generate a high-frequency output signal.

In some embodiments, the power-supply/controller module 446 may include one or more amplifiers adapted to operate at 915 MHz, 2.45 GHz and/or 5.1 GHz. In some embodiments, the power-supply/controller module 446 may include a solid-state amplifier having one or more high-frequency switching elements. The one or more high-frequency switching elements may include one or more Gallium Nitride Metal-Oxide Semiconductor Field-Effect Transistors (GaN MOSFETs). Power-supply/controller module 446 may include logic, circuitry and/or code adapted to control a self-contained power source, amplifier, and/or signal generator responsive to one or more electrical signals received from one or more temperature sensors, singly or in conjunction with one or more electrical signals received from one or more other sensor devices (e.g., sensor devices adapted to detect blood pressure, pulse pressure, mean arterial pressure, and/or pulse rate, sensor devices adapted to sense respiratory rate, sensor devices adapted to sense pulse oximetry and/or arterial pulse).

Body-enclosing garment 431 may include one or more groups or arrays of energy-delivery elements operable to emit energy absorbable into the body of the wearer. In some embodiments, as shown in FIG. 4, the energy-delivery elements of the body-enclosing garment 431 are configured as four energy-delivery element arrays 421, 422, 423 and 424, longitudinally extending along the wearer height. In some embodiments, one or more vital sign detectors may be disposed in association with one or more energy-delivery element arrays, or portions thereof, and the power-supply/controller module 446 may be configured to active and deactivate one or more energy-delivery element arrays, or portions thereof, and/or adjust one or more operating parameters associated with a signal generator and/or amplifier responsive to one or more signals received from one or more vital sign detectors.

In some embodiments, the power-supply/controller module 446 and/or other circuitry may be adapted to adjust one or more operating parameters associated with the signal generator and/or perform other control functions, alarming functions, or other functions in association therewith. The power-supply/controller module 446 may be adapted to monitor one or more vital sign sensors and/or generate a measure of the core body temperature based, at least in part, on one or more electrical signals received from one or more sensors. In some embodiments, the power-supply/controller module 446 may be configured to selectively control the energy-delivery element arrays 421, 422, 423 and 424, or portions thereof, e.g., to deliver energy over one or more regions of the wearer, responsive to one or more electrical signals received from one or more temperature sensors. The power-supply/controller module 446 may additionally, or alternatively, be configured to selectively control the energy-delivery element arrays 421, 422, 423 and 424, or portions thereof, e.g., to deliver energy over one or more regions of the wearer, responsive to one or more electrical signals indicative of measurement of respiratory rate, pulse rate, pulse pressure, pulse oximetry and/or blood pressure.

In some embodiments, the power-supply/controller module 446 and/or other circuitry may be adapted to adjust one or more energy-delivery parameters based, at least in part, on one or more electrical signals received from one or more vital sign detectors. Some examples of energy-delivery parameters include the duration of application of electromagnetic energy by the one or more energy-delivery elements (or groups or arrays of energy-delivery elements), the power level of energy delivered to one or more regions of the body-enclosing garment 431 and/or other energy-delivery apparatus (e.g., hood 670 shown in FIG. 7). The power-supply/controller module 446 may additionally, or alternatively, be adapted to adjust the level to which core body temperature is raised and/or the rate of increase in core body temperature, e.g., responsive to one or more electrical signals received from one or more vital sign detectors.

Figure 5:
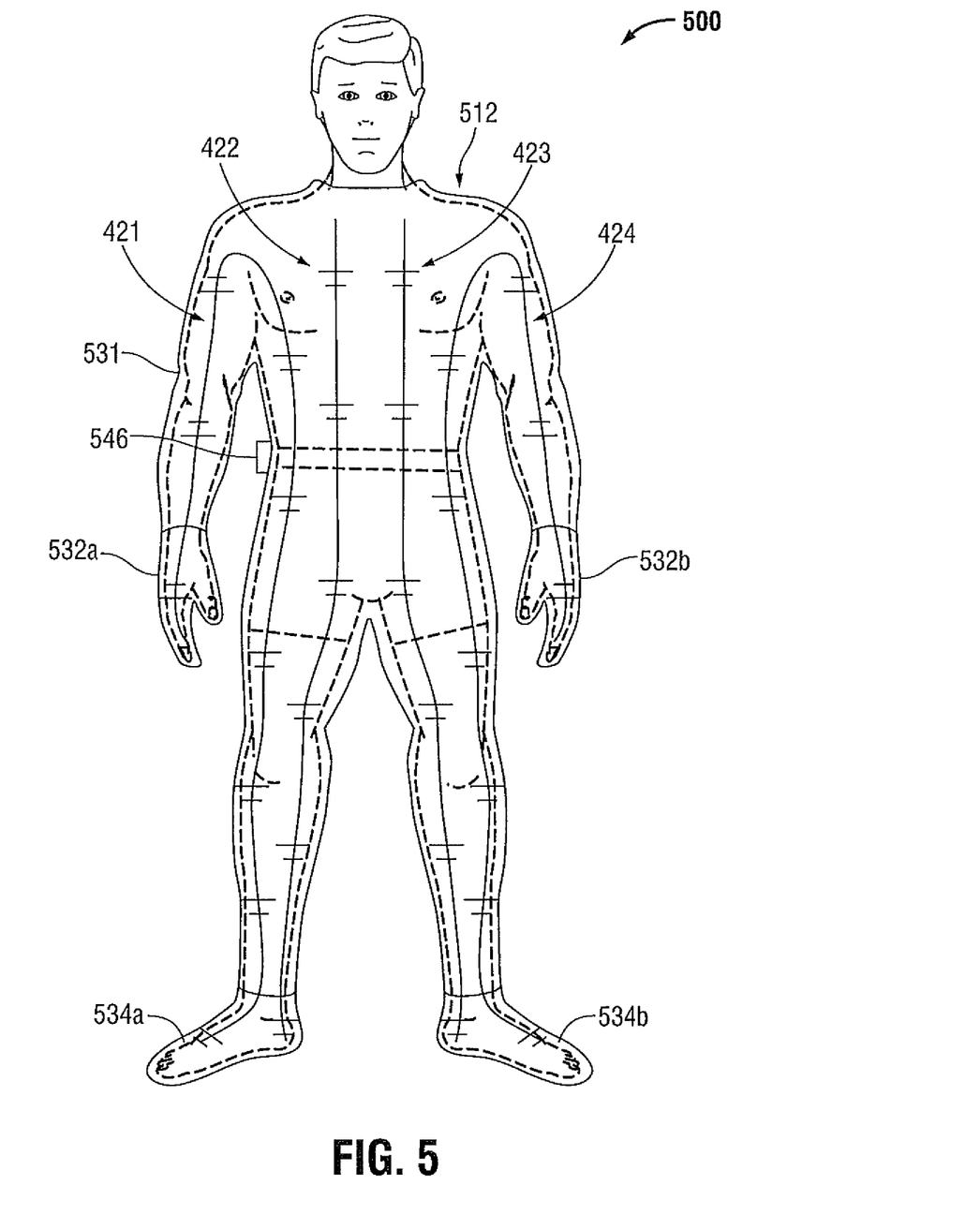
FIG. 5 is a schematic diagram of a system including the body-enclosing garment of FIG. 4, shown with hand-enclosure portions and foot-enclosure portions being adapted to radiate electromagnetic energy to provide warmth to the hands and feet of the wearer, in accordance with an embodiment of the present disclosure.

FIG. 5 shows a system (shown generally as 500) including a body-enclosing garment 531 adapted to radiate electromagnetic energy for warming the wearer in accordance with an embodiment of the present disclosure. Body-enclosing garment 531 includes an energy-applicator device 512 including a configuration of energy-delivery elements integrated into the body-enclosing garment 531. In some embodiments, the body-enclosing garment 531 is adapted to controllably emit a near-field standing wave of energy absorbable into the body of the wearer.

Body-fitting member 531 may be formed of one or more layers of any suitable material to enclose the torso, arms and legs, and may be configured to allow for fitting over clothes. In some embodiments, the body-enclosing garment 531 may have a single-layer or multi-layer construction to provide physical protection to the wearer. Body-enclosing garment 531 of FIG. 5 is similar to the body-enclosing garment 431 shown in FIG. 4, except that the body-enclosing garment 531 includes hand-enclosure portions 532a, 532b and foot-enclosure portions 534a, 534b. In some embodiments, the hand-enclosure portions 532a, 532b are adapted to radiate electromagnetic energy for warming the hands of the wearer, and foot-enclosure portions 534a, 53 may be adapted to radiate electromagnetic energy for warming the feet of the wearer. For ease of explanation and understanding, the body-enclosing garment 531 shown in FIG. 5 is configured with the energy-delivery element arrays 421, 422, 423 and 424 of the energy-applicator device 412 shown in FIG. 4; however, it is to be understood that the body-enclosing garment 531 may include fewer or additional energy-delivery elements than the body-enclosing garment 431 shown in FIG. 3.

In some embodiments, the hand-enclosure portions 532a, 532b may be adapted to be removeably coupleable to arm portions of the body-enclosing garment 531. Hand-enclosure portions 532a, 532b may be adapted to radiate electromagnetic energy, and may include one or more electrical connectors suitable for making an electrical connection with the energy-delivery element arrays 421, 422, 423 and/or 424. In some embodiments, the hand-enclosure portions 532a, 532b may be integrally formed with the body-enclosing garment 531.

In some embodiments, the foot-enclosure portions 534a, 534b may be adapted to be removeably coupleable to leg portions of the body-enclosing garment 531. Foot-enclosure portions 534a, 534b may be adapted to radiate electromagnetic energy, and may include one or more electrical connectors suitable for making an electrical connection with the energy-delivery element arrays 421, 422, 423 and/or 424. In some embodiments, the foot-enclosure portions 534a, 534b may be integrally formed with the body-enclosing garment 531. Foot-enclosure portions 534a, 534b may be configured to allow for fitting over footwear.

System 500 includes a power-supply/controller module 546 operably associated with the energy-applicator device 512. Power-supply/controller module 546 may be attached, coupled to, or otherwise associated with, the body-enclosing garment 531. Power-supply/controller module 546 is similar to the power-supply/controller module 446 shown in FIG. 4, and further description thereof is omitted in the interests of brevity.

Figure 6:
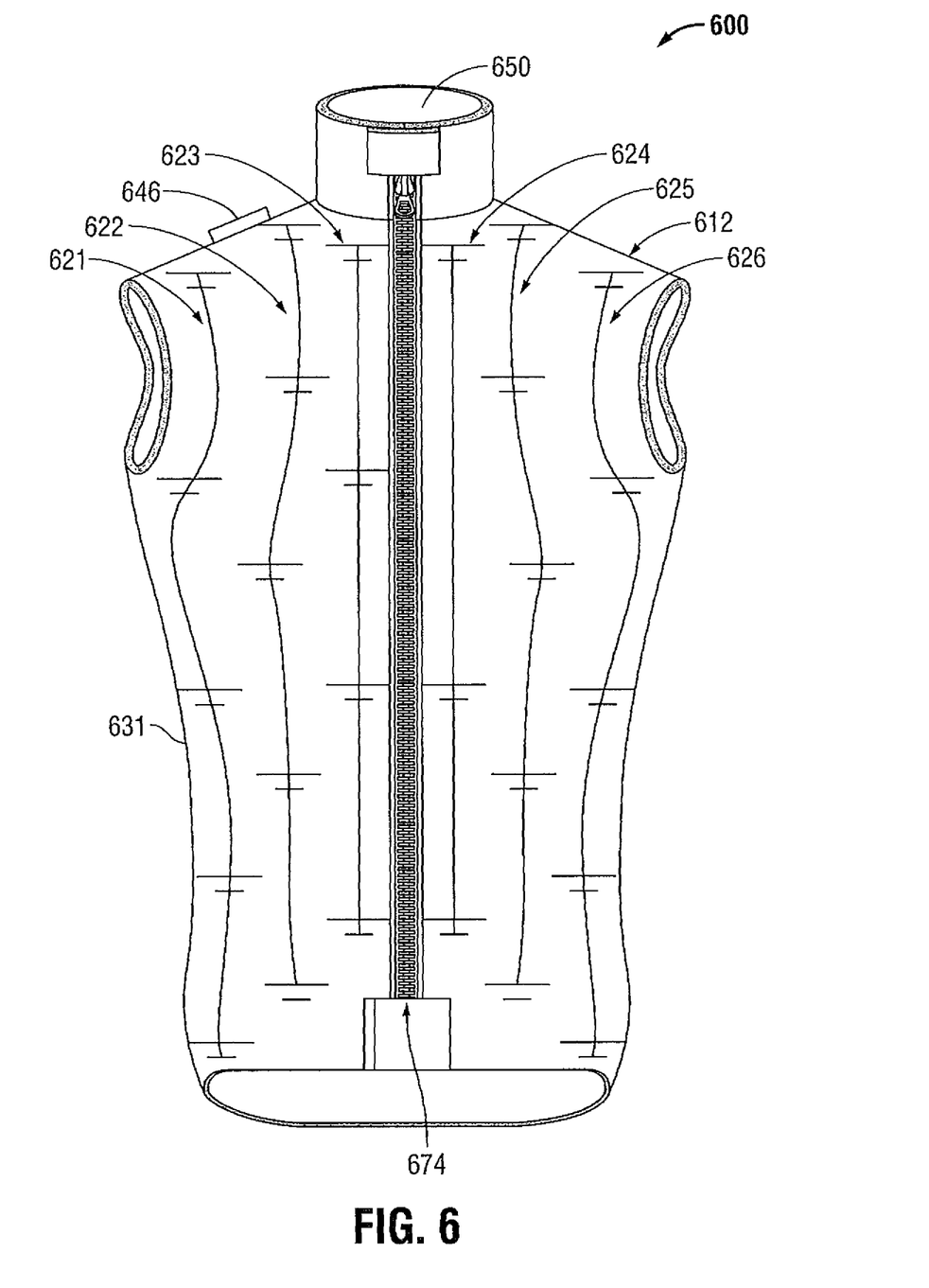
FIG. 6 is a schematic diagram of a system including a torso-enclosing garment adapted to radiate electromagnetic energy for warming the wearer in accordance with an embodiment of the present disclosure.

FIG. 6 shows a system (shown generally as 600) including a torso-enclosing garment 631 adapted to radiate energy, e.g., electromagnetic energy, for warming the wearer in accordance with an embodiment of the present disclosure. The torso-enclosing garment 631 includes an energy-applicator device 612 including a configuration of energy-delivery elements integrated into the torso-enclosing garment 631. In some embodiments, the torso-enclosing garment 631 is adapted to controllably emit a near-field standing wave of energy absorbable into the body of the wearer.

The torso-enclosing garment 631 may include one or more layers of dielectric material covering the core or torso of the body. In some embodiments, dielectric materials used to form the torso-enclosing garment 631 may vary in dielectric constant, e.g., to aid in radiation directivity and impedance matching and/or to achieve the optimum energy to tissue delivery. In some embodiments, as shown in FIG. 6, the torso-enclosing garment 631 is configured into a sleeveless, legless garment including a zippered fastener 674.

System 600 includes a power-supply/controller module 646 operably associated with the energy-applicator device 612. Power-supply/controller module 546 may be attached, coupled to, or otherwise associated with, the torso-enclosing garment 631. Power-supply/controller module 646 is similar to the power-supply/controller module 446 shown in FIG. 4, and further description thereof is omitted in the interests of brevity.

The torso-enclosing garment 631 may include one or more groups or arrays of energy-delivery elements operable to emit energy absorbable into the body of the wearer. In some embodiments, as shown in FIG. 6, the energy-delivery elements of the torso-enclosing garment 631 are configured as six energy-delivery element arrays 621, 622, 623 and 624, longitudinally extending along the wearer height. In some embodiments, the energy-delivery elements (or energy-delivery element arrays) may be disposed between the same or different layers of dielectric material. Energy-applicator device 612 may include one or more connector portions (not shown) provided with one or more electrical connectors or terminals suitable for making electrical connections with certain of the circuitry of the power-supply/controller module 646.

In some embodiments, one or more vital sign detectors may be disposed in association with one or more energy-delivery element arrays, or portions thereof, and the power-supply/controller module 646 may be configured to active and deactivate one or more energy-delivery element arrays, or portions thereof, and/or adjust one or more operating parameters associated with a signal generator and/or amplifier, e.g., associated with the power-supply/controller module 646, responsive to one or more signals received from one or more vital sign detectors, e.g., sensor devices adapted to detect blood pressure, pulse pressure, mean arterial pressure, and/or pulse rate, sensor devices adapted to sense respiratory rate, sensor devices adapted to sense pulse oximetry and/or arterial pulse.

Figure 7:
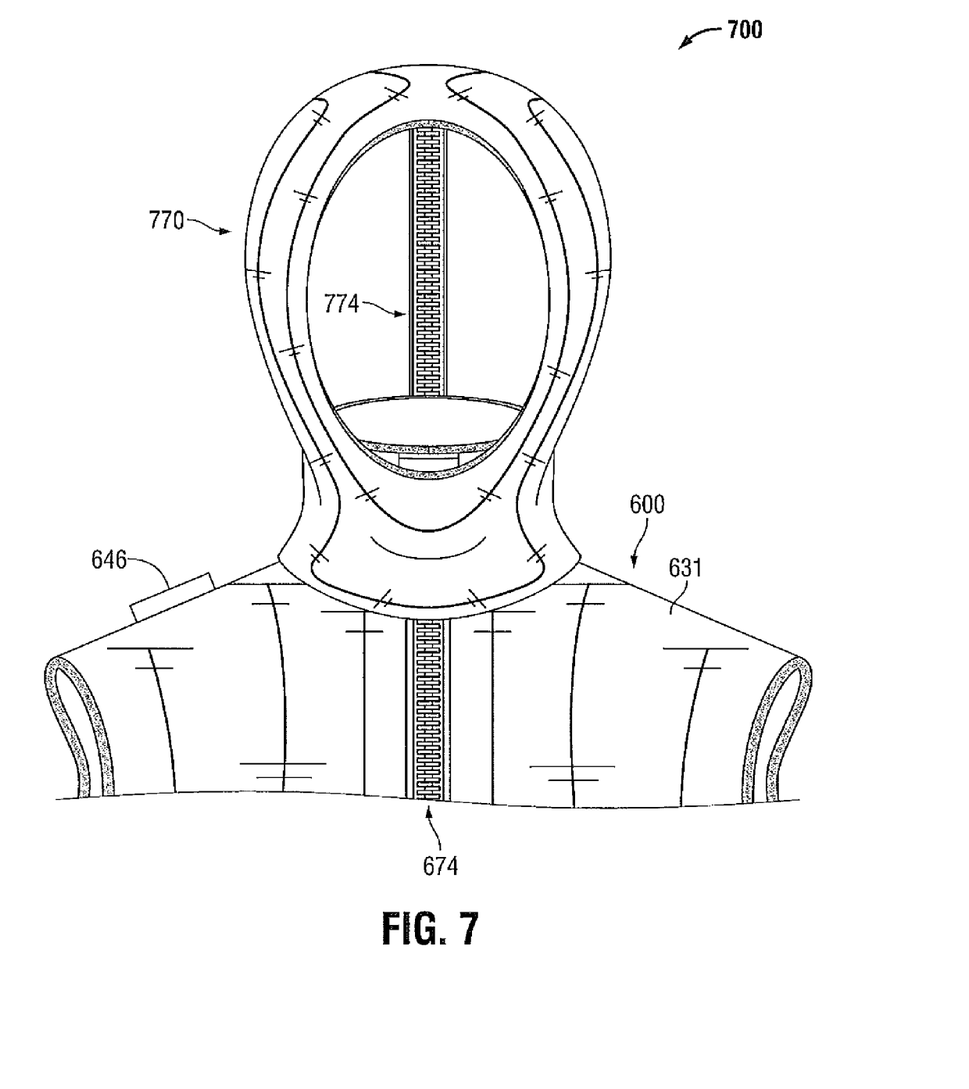
FIG. 7 is a schematic diagram of a system including a head garment adapted to radiate electromagnetic energy for warming the wearer in accordance with an embodiment of the present disclosure.

FIG. 7 shows a system including a head garment 770 adapted to radiate energy, e.g., electromagnetic energy, for warming the wearer in accordance with an embodiment of the present disclosure. The head garment 770 may include one or more groups or arrays of energy-delivery elements operable to emit energy absorbable into the body of the wearer. The head garment 770 may be formed of any suitable conformable material that allows the energy-delivery elements to radiate electromagnetic energy to the treatment region, and may have a single-layer or multi-layer construction. In some embodiments, one or more vital sign detectors may be disposed in association with one or more energy-delivery element arrays, or portions thereof, associated with the head garment 770.

In some embodiments, the head garment 770 may include one or more layers of dielectric material, and may include a zippered fastener 774. In some embodiments, the head garment 770 may be integrally connected to the torso-enclosing garment 631 shown in FIG. 6. The head garment 770 may include one or more connector portions (not shown) provided with one or more electrical connectors or terminals suitable for making electrical connections with certain of the circuitry of the power-supply/controller module 646.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A system for the treatment of hypothermia, comprising:
an energy source configured to output energy;
a controller coupled to the energy source;
an encasing-structure configured to enclose at least a torso, arms, and legs of a patient;
an energy-applicator device including a configuration of energy-delivery elements disposed in association with the encasing-structure, the energy-delivery elements being configured to controllably emit a near-field standing wave of energy absorbable into the torso, arms, and legs of the patient to increase core body temperature of the patient; and
a vital sign detector configured to generate an electrical signal indicative of a measurement of a vital sign of the patient;
wherein the controller is configured to receive the electrical signal from the vital sign detector and to adjust a treatment parameter based at least in part on the electrical signal.

2. The system of claim 1, wherein at least one operating parameter associated with the energy source is adjusted based at least in part on the electrical signal.

3. The system of claim 2, wherein the at least one operating parameter associated with the energy source is selected from the group consisting of temperature, impedance, power, current, voltage, mode of operation, and duration of application of energy.

4. The system of claim 1, wherein the energy-delivery elements are integrated into the encasing-structure.

5. The system of claim 1, wherein the vital sign detector includes a first sensor device and a second sensor device.

6. The system of claim 5, wherein the first sensor device is configured to sense a temperature of the patient to facilitate feedback-control of emitted energy.

7. The system of claim 6, wherein the second sensor device is configured to sense an arterial pulse of the patient to facilitate feedback-control of emitted energy.

8. The system of claim 6, wherein the second sensor device is configured to detect a blood pressure of the patient to facilitate feedback-control of emitted energy.

9. The system of claim 5, wherein the first sensor device is disposed on a first portion of the encasing-structure and is configured to sense a temperature of a first region of the patient, the second sensor device being disposed on a second portion of the encasing-structure and configured to sense a temperature of a second region of the patient, the second region being different than the first region.

10. The system of claim 5, wherein at least one of the first sensor device or the second sensor device is a Hall effect sensor.

11. The system of claim 1, wherein the vital sign detector is configured to sense an arterial pulse of the patient to facilitate feedback-control of emitted energy.

12. The system of claim 1, wherein the vital sign detector is configured to sense a mean arterial pressure of the patient to facilitate feedback-control of emitted energy.

13. The system of claim 1, wherein the vital sign detector is configured to sense a pulse oximetry of the patient to facilitate feedback-control of emitted energy.

14. The system of claim 1, wherein the vital sign detector is adapted configured to detect a blood pressure of the patient to facilitate feedback-control of emitted energy.

15. The system of claim 1, wherein the vital sign detector is configured to detect at least one of:
 a change in a core body temperature of the patient; or
 a rate of change in a core body temperature of the patient.

16. The system of claim 1, wherein each of the energy-delivery elements extend longitudinally along a length of the encasing-structure and are laterally spaced relative to one another along a width of the encasing-structure.

17. A system, comprising:
 a controller coupled to a signal generator;
 a body-enclosing garment configured to enclose at least a torso, arms, and legs of a wearer and to controllably emit energy for warming at least the torso, arms, and legs of the wearer, wherein the body-enclosing garment includes:
  an energy-applicator device including a configuration of an energy-delivery element array disposed in association with the body-enclosing garment to apply energy to the torso, arms, and legs of the wearer; and
  hand-enclosure portions configured to radiate energy to provide warmth to hands of the wearer; and
 a plurality of vital sign detectors, wherein each one of the plurality of vital sign detectors is configured to generate an electrical signal indicative of a measurement of a vital sign of the wearer;
 wherein the controller is configured to receive the electrical signals from the plurality of vital sign detectors and to selectively control the energy-delivery element array to deliver energy over at least the torso, legs, and arms of the wearer based at least in part on the electrical signals received from the plurality of vital sign detectors.

18. The system of claim 17, wherein the energy-delivery element array is integrated into the body-enclosing garment.

* * * * *